United States Patent [19]

Kisalus

[11] Patent Number: 5,334,569
[45] Date of Patent: Aug. 2, 1994

[54] ALKYLATION AID

[75] Inventor: John C. Kisalus, Houston, Tex.

[73] Assignee: Nalco Chemical Company, Naperville, Ill.

[21] Appl. No.: 62,738

[22] Filed: Jun. 15, 1987

Related U.S. Application Data

[63] Continuation-in-part of Ser. No. 17,961, Feb. 24, 1987, abandoned.

[51] Int. Cl.⁵ .............................................. B01J 31/04
[52] U.S. Cl. ................................... 502/167; 502/150; 502/208; 502/216; 502/224; 558/70; 564/463
[58] Field of Search ............... 585/709, 711, 721, 725; 564/463; 502/167, 162, 150, 208, 216, 224; 558/70

[56] References Cited

U.S. PATENT DOCUMENTS

| | | | |
|---|---|---|---|
| 3,663,648 | 5/1972 | Ruble | 585/711 |
| 3,865,896 | 2/1975 | McCoy et al. | 585/725 |
| 3,870,765 | 3/1975 | McCoy et al. | 585/725 |
| 4,467,132 | 8/1984 | Go et al. | 585/731 |
| 4,544,794 | 10/1985 | Miller et al. | 585/730 |
| 4,560,825 | 12/1985 | Kramer et al. | 585/730 |
| 5,073,674 | 12/1991 | Olah | 585/721 |

*Primary Examiner*—Anthony McFarlane
*Attorney, Agent, or Firm*—Robert A. Miller; Joseph B. Barrett; James J. Drake

[57] ABSTRACT

Alkylation catalyst of the type used in the refining of petroleum can be improved by using a promoter composition which contains an alkyl phosphate ester amine salt and pinene.

4 Claims, No Drawings

ALKYLATION AID

This application is a continuation-in-part of Ser. No. 017,961, filed Feb. 24, 1987, now abandoned.

The alkylation of $C_4$-$C_6$ aliphatic hydrocarbons by $C_3$-$C_5$ olefins is a well-known commercial process. Commonly, an aliphatic hydrocarbon such as isobutane is reacted in the liquid phase with a mixture of light olefins in the presence of a heterogeneous, liquid phase strong acid catalyst. The strong acid catalyst might be sulfuric acid, hydrofluoric acid, phosphoric acid or any other suitable strong acid. The products formed from the strong acid catalyzed reaction of isoparaffins with lower olefins are useful as gasoline blending components.

PRIOR ART

In the strong acid catalyzed alkylation process, involving paraffinic hydrocarbons and lower olefin hydrocarbons, use of promoters to improve the efficiency of the said process has been attempted. Some of these attempts include the use of adamantane derivatives (U.S. Pat. No. 4,560,825, Kramer, et al) and long chain neo acids (U.S. Pat. No. 4,544,794, Miller, et al).

SUMMARY OF THE INVENTION

In its most general embodiment, the invention comprises an alkylation process which comprises contacting an alkylatable paraffinic hydrocarbon and an olefinic alkylating agent under alkylation conditions with a catalyst composition comprising a strong acid in the presence of a promoter. The promoter comprises from 5-85% by weight of oil-soluble $C_8$-$C_{24}$ tertiary alkyl primary amine salts of $C_6$-$C_{22}$ mono- and di-alkyl phosphate esters, from 5-55% by weight of either alpha or beta pinene and with the balance of said promoter being a hydrocarbon solvent.

As can be seen from the above description, the promoter composition of the invention contains two active ingredients, e.g. the amine salts of mono- and di-alkyl phosphate esters, and secondly the alpha or beta pinene.

The promoter of this invention effects the process in the following manner:

The surface active component of the additive lowers the interfacial surface tension between the hydrocarbon feed and the sulfuric acid catalyst, thus increasing the efficiency of the mechanical mixer or turbine in forming an emulsion between the two phases. The hydride transfer catalyst, e.g. the pinene, in the additive increases the rate of hydride transfer across the interface of the acid catalyst and hydrocarbon feed. Hydride transfer across the interface is theorized by many to be the rate-determining step in the alkylation of alkanes with olefins in the presence of a strong acid catalyst. The final effect of the additive in the alkylation unit is to improve the resolution of the two phases once the acid/hydrocarbon emulsion goes to the acid settler. The emulsion breaking effect helps lower acid consumption by preventing acid carryover in the form of a rag layer.

THE OIL-SOLUBLE MONO- AND DI-ALKYL PHOSPHATE ESTER AMINE SALTS

The mono- and di-alkyl phosphate esters used in the practice of the invention are conveniently prepared by reacting an appropriate alcohol with $P_2O_5$. Alternatively, phosphoric acid may be esterified directly although this is not desirable from the standpoint of yield and cost. The mono- and di-alkyl phosphate esters generally contain alkyl radicals which contain from 6 to 22 carbon atoms in a straight or branched chain configuration. Preferably, it is preferred to employ $C_6$-$C_{12}$ branched chain phosphate esters with preferred esters being mono-and di-isooctyl phosphate esters.

The amine used to prepare the salts of the above described phosphate esters should be a tertiary alkyl primary amine containing from 8-24 carbon atoms.

A particularly preferred class of amines are tertiary-alkyl primary amines. The tertiary-alkyl primary amines have the formula:

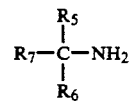

More specifically, the tertiary-alkyl primary amine constitutes a component wherein $R_5$ and $R_6$ are lower alkyl groups, usually methyl groups, and $R_7$ constitutes a long chain alkyl radical composed of 8 to 19 carbons. Tertiary-alkyl primary amines which have been found eminently suitable for the instant invention are "Primene 81-R" and "Primene JM-T". "Primene 81-R" is reported by its manufacture to be composed of principally tertiary-alkyl primary amines having 11-14 carbons and has a molecular weight principally in the range of 171-213, a specific gravity at 25° C. of 0.813, a refractive index of 1.423 at 25° C. and a neutralization equivalent of 191. "Primene Jm-T" is reported by the manufacturer to be composed of tertiary-alkyl primary amines having 18-22 carbons with a molecular weight principally in the range of 269-325, a specific gravity at 25° C. of a refractive index of 1.456 and a neutralization equivalent of 311.

The primary constituent of "Primeme 81-R" is reported to be:

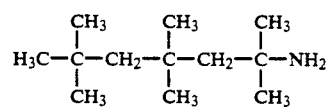

the primary constituent of "Primene JM-T" is reported to be essentially the same structure as "Primene 81-R", but with 22 carbons. "Primene" is a trademark of the Rohm & Haas Company for its brand of tertiary alkyl primary amines.

Of the above described amines, "Primene 81-R" is preferred. To prepare commercial products and to form the mono-and di-alkyl phosphate ester amine salts, it is convenient to employ a hydrocarbon liquid solvent for the preparation of the amine salt. The solvent can then also function as a carrier when the amine salts are combined with the alpha or beta pinene. Salt formation may occur at room temperature or can be accomplished during mild heating conditions.

The hydrocarbon solvent may be selected from a single hydrocarbon liquid or a blend thereof capable of dissolving the ingredients which form the promoter composition. Preferred hydrocarbon liquid solvents are the so-called aromatic solvents which are a blend of aromatics which are formed from the refining of petroleum. Theses are sometimes referred to as heavy aromatic solvents. A typical aromatic heavy solvent is the following:

This product can be defined as a heavy aromatic solvent naphtha (petroleum). It consists predominantly of C9–C11 aromatic hydrocarbons, primarily C10. This product contains naphthalene at approximately 9 mass percent.

Although less desirable, conventional aromatic compounds such as benzene, xylene and toluene may be used. To illustrate typical promoter compositions used in the practice of the invention, the following are given by way of illustration:

|  | Weight Percent |
|---|---|
| Phosphate Ester Amine Salts | |
| General Range | 5–85 |
| Preferred Range | 40–60 |
| Most Preferred Range | 50 |
| Alpha or Beta Pinene | |
| General Range | 5–55 |
| Preferred Range | 20–40 |
| Most Preferred Range | 30 |
| Hydrocarbon Solvent | |
| General Range | Balance |
| Preferred Range | Balance |
| Most Preferred Range | Balance |

A typical composition of the invention, hereafter Composition I, would contain 50 percent by weight of amine salts of mono- and di-isooctyl phosphate esters, 30% is alpha pinene with a balance being a heavy aromatic solvent.

DOSAGE

The promoting compositions of the invention are added to the ingredients being alkylated and the catalyst to provide a dosage within the range of 10–2,000 ppm by volume based on catalyst volume and a 100% active promoter. A preferred dosage range is 100 to 2,000 ppm by volume based on catalyst volume and a 100% active promoter.

FIELD TESTS

The test method used generally corresponds to that described in Examples I and II of U.S. Pat. No. 4,467,132, the disclosure of which is incorporated herein by reference.

The specifics of the test conditions are set forth below:

10,000 BPD alkylation unit
Isobutane/mixed butene ratio of 8:1
Spent sulfuric strength 91.5%, fresh acid 99%
Temperature 50°–60° F.
Acid consumption for "before"=0.80 lbs./gallon of alkylate
Acid consumption for "after" with 200 ppm additive=0.69 lbs./gallon of alkylate The results are presented in Table I.

TABLE I

| Trial Process Parameter | Base Case Average | Composition I Trial Average |
|---|---|---|
| Alkylate Production BBLS/DAY | 9152 | 9928 |
| Fresh Acid Used BBLS/DAY | 496 | 451 |
| Acid Consumption # Acid/Gal. Alk. | 0.80 | 0.69 |
| Spent Acid Strength (%) | 91.5 | 91.3 |
| Contactor Temperature (°F.) | 58.7 | 58.5 |
| Number of Contactors in Service | 5.48 | 4.96 |
| Contactor Seed (RPM) | 2956 | 2993 |
| Isobutane/Olefin Ratio | 8.68 | 8.52 |
| Butadiene Concentration (%) | 0.12 | 0.15 |
| $C_3$ Olefin Concentration (%) | 1.0 | 1.7 |
| Additive Concentration (ppm) | — | 200 |

Having thus described my invention, it is claimed:

1. A promoter composition useful in a strong acid catalyzed alkylation process, the promoter comprising from 5–8% by weight of an oil-soluble $C_8$–$C_{24}$ tertiary alkyl primary amine salt of a mixed $C_8$–$C_{22}$ mono- and di-alkyl phosphate ester, from 5–55% by weight of either alpha or beta primene and with the balance of said promoter being a hydrocarbon solvent.

2. The promoter composition of claim 1 where the tertiary alkyl primary amine has 11–14 carbon atoms, wherein the mono- and di-alkyl portion of the phosphate ester contains between $C_6$–$C_{12}$ branched chain alkyl groups, the tertiary alkyl primary amine salt of the dialkyl phosphate ester is present in the amount ranging from 40–60% by weight, and the alpha or beta pinene is present in the amount of 20–40%.

3. The promoter composition of claim 1 where the promoter has the following composition:
   50% by weight of $C_{11}$–$C_{14}$ tertiary alkyl primary amine salt of mono- and di-octyl phosphate esters, 30% by weight of alpha pinene and with the balance being an aromatic hydrocarbon solvent.

4. An organic salt comprising the oil-soluble $C_8$–$C_{24}$ tertiary alkyl primary amine salt of a mixed $C_6$–$C_{22}$ mono- and di-alkyl phosphate ester.

* * * * *